(12) United States Patent
Kosaraju et al.

(10) Patent No.: US 11,883,784 B2
(45) Date of Patent: Jan. 30, 2024

(54) MICROPOROUS MEMBRANE AND METHODS TO MAKE SAME

(71) Applicant: Fresenius Medical Care Holdings, Inc., Waltham, MA (US)

(72) Inventors: Praveen Kosaraju, Farmington, UT (US); Monica P. Hall, Ogden, UT (US); Jiunn Teo, Pleasant View, UT (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 81 days.

(21) Appl. No.: 17/239,715

(22) Filed: Apr. 26, 2021

(65) Prior Publication Data

US 2021/0245108 A1  Aug. 12, 2021

Related U.S. Application Data

(62) Division of application No. 16/125,880, filed on Sep. 10, 2018, now Pat. No. 11,014,051.

(Continued)

(51) Int. Cl.
*B01D 67/00* (2006.01)
*A61M 1/16* (2006.01)
(Continued)

(52) U.S. Cl.
CPC .......... *B01D 67/0016* (2013.01); *A61M 1/16* (2013.01); *A61M 1/34* (2013.01); *A61M 1/3666* (2013.01);
(Continued)

(58) Field of Classification Search
CPC ............... B01D 67/0016; B01D 61/14; B01D 67/0088; B01D 69/02; B01D 69/06;
(Continued)

(56) References Cited

U.S. PATENT DOCUMENTS 3,615,024 A   10/1971  Michaels
3,691,068 A    9/1972  Cross
(Continued)

FOREIGN PATENT DOCUMENTS

CN   1233191 A   10/1999
CN   1704152 A   12/2005
(Continued)

OTHER PUBLICATIONS

Office Action issued in corresponding Japanese Patent Application No. 2020-514549 dated Jan. 4, 2022 (with English translation) (11 pages).
(Continued)

*Primary Examiner* — Pranav N Patel
(74) *Attorney, Agent, or Firm* — Kilyk & Bowersox, P.L.L.C.

(57) ABSTRACT

A method is disclosed for forming a microporous membrane that incorporates an additive having low water solubility at the membrane's active surface from a precipitation fluid. The incorporated additive at the membrane's active surface can improve one or more of the membrane's hydrophilicity, wettability, anti-fouling behavior, blood compatibility, and stability over long periods of use or repetitive use. The microporous membrane with this modified active surface can be a hollow fiber, flat sheet, or other self-supporting shape. The microporous membranes can be used for membrane filtering or a solute and/or solvent exchange process, which involve contacting aqueous-based fluid or blood with the microporous membrane, such processes for dialysis, blood oxygenation, or blood separation filtering, or other processes.

23 Claims, 5 Drawing Sheets

Related U.S. Application Data

(60) Provisional application No. 62/556,517, filed on Sep. 11, 2017.

(51) Int. Cl.

| | | |
|---|---|---|
| *A61M 1/34* | (2006.01) | |
| *B01D 61/14* | (2006.01) | |
| *B01D 69/02* | (2006.01) | |
| *A61M 1/36* | (2006.01) | |
| *B01D 69/06* | (2006.01) | |
| *B01D 69/08* | (2006.01) | |
| *B01D 71/08* | (2006.01) | |
| *B01D 71/40* | (2006.01) | |
| B01D 65/08 | (2006.01) | |
| B01D 61/24 | (2006.01) | |
| B01D 71/54 | (2006.01) | |
| B01D 71/68 | (2006.01) | |

(52) U.S. Cl.
CPC ......... *B01D 61/14* (2013.01); *B01D 67/0088* (2013.01); *B01D 69/02* (2013.01); *B01D 69/06* (2013.01); *B01D 69/087* (2013.01); *B01D 71/08* (2013.01); *B01D 71/40* (2013.01); *A61M 2207/00* (2013.01); *B01D 61/243* (2013.01); *B01D 65/08* (2013.01); *B01D 71/54* (2013.01); *B01D 71/68* (2013.01); *B01D 2323/02* (2013.01); *B01D 2325/28* (2013.01); *B01D 2325/36* (2013.01)

(58) Field of Classification Search
CPC ...... B01D 69/087; B01D 71/08; B01D 71/40; B01D 61/243; B01D 65/08; B01D 71/54; B01D 71/68; B01D 2323/02; B01D 2325/28; B01D 2325/36; A61M 1/16; A61M 1/34; A61M 1/3666; A61M 2207/00

See application file for complete search history.

(56) References Cited

U.S. PATENT DOCUMENTS

| | | | |
|---|---|---|---|
| 4,051,300 | A | 9/1977 | Klein et al. |
| 4,900,449 | A | 2/1990 | Kraus et al. |
| 4,906,375 | A | 3/1990 | Heilmann |
| 5,232,597 | A | 8/1993 | Eguchi |
| 5,340,480 | A | 8/1994 | Kawata et al. |
| 5,800,412 | A | 9/1998 | Zhang et al. |
| 5,911,880 | A | 6/1999 | Klein et al. |
| 8,092,815 | B2 | 1/2012 | Sabesan |
| 2004/0045897 | A1 | 3/2004 | Nakabayashi et al. |
| 2007/0205155 | A1* | 9/2007 | Babcock ............... B01D 61/28 422/534 |
| 2010/0323573 | A1* | 12/2010 | Chu ................... B01D 69/141 977/773 |
| 2011/0045041 | A1* | 2/2011 | Golubovic-Liakopoulos ............. A61P 17/02 514/474 |
| 2011/0263020 | A1 | 10/2011 | Zweigart et al. |
| 2012/0074063 | A1 | 3/2012 | Krause et al. |
| 2012/0175300 | A1* | 7/2012 | Herron ................. B01D 71/16 210/500.27 |
| 2013/0306544 | A1 | 11/2013 | Jeno et al. |
| 2015/0209735 | A1 | 6/2015 | Hara et al. |
| 2019/0076787 | A1 | 3/2019 | Kosaraju et al. |

FOREIGN PATENT DOCUMENTS

| | | |
|---|---|---|
| CN | 101406812 A | 4/2009 |
| CN | 102019150 A | 4/2011 |
| EP | 0749775 A1 | 12/1996 |
| EP | 2774635 A1 | 9/2014 |
| JP | 9-29232 A | 2/1997 |
| JP | H0966225 A | 3/1997 |
| JP | 2000308814 A | 11/2000 |
| JP | 2010248092 A | 11/2010 |
| JP | 2012527341 A | 11/2012 |
| JP | 5426283 B2 | 2/2014 |
| JP | 2015226902 A | 12/2015 |
| WO | 9920378 A1 | 4/1999 |
| WO | 0242530 A1 | 5/2002 |
| WO | 2006012453 A1 | 2/2006 |
| WO | 2011110441 A2 | 9/2011 |
| WO | 2012091028 A1 | 7/2012 |
| WO | 2014170391 A1 | 10/2014 |
| WO | 2016178835 A1 | 11/2016 |
| WO | 2016184945 A1 | 11/2016 |

OTHER PUBLICATIONS

Office Action issued in corresponding Chinese Patent Application No. 201880058317.7 dated Jul. 27, 2022 (with English translation) (21 pages).
Guo et al., "Hematodialysis," Apr. 30, 2016 (relevance set forth in English translation of Chinese Office Action submitted herewith).
Hu et al., "Process for synthesizing and producing new Polymer," May 31, 2014 (relevance set forth in English translation of Chinese Office Action submitted herewith).
Office Action issued in corresponding European Patent Application 18782246.5 dated Nov. 23, 2022 (5 pages).
Ye et al., "In situ modification on cellulose acetate hollow fiber membrane modified with phospholipid polymer for biomedical application," Mar. 1, 2005, Journal of Membrane Science, vol. 249, pp. 133-141.
Office Action issued in corresponding Japanese Patent Application No. 2020-514549 dated Mar. 30, 2021 (with partial English translation) (11 pages).
Office Action issued in corresponding Japanese Patent Application No. 2020-514549 dated Apr. 6, 2021 (with partial English machine translation) (11 pages).
Lopez-Donaire, "Surface Modifying Oligomers Used to Functionalize Polymeric Surfaces: Consideration of Blood Contact Applications," Journal of Applied Polymer Science, 2014, pp. 1-15, DOI: 10.1002/APP.40328.
International Search Report and Written Opinion issued in corresponding International Patent Application No. PCT/US2018/050139 dated Jan. 18, 2019 (14 pages).

* cited by examiner

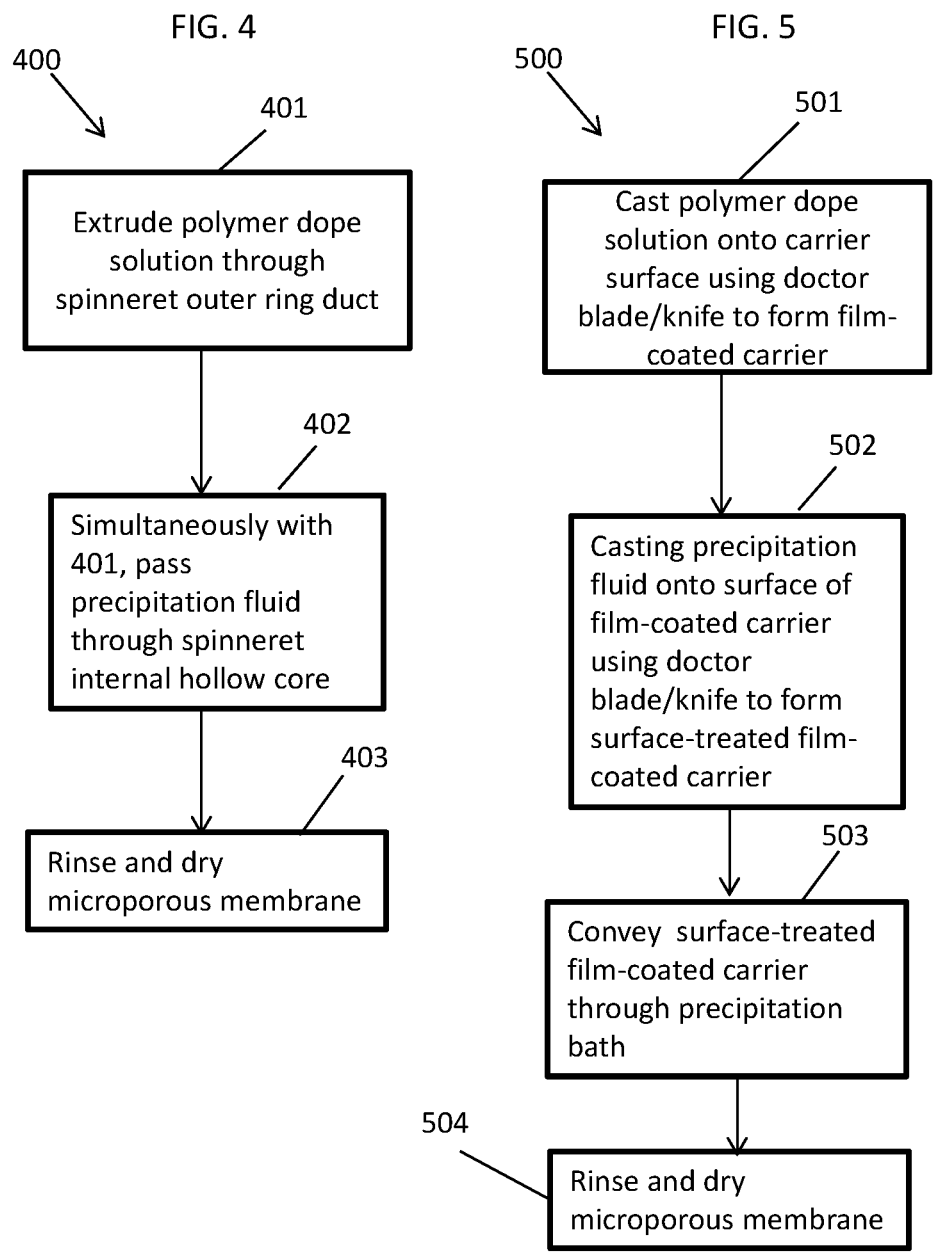

MICROPOROUS MEMBRANE AND METHODS TO MAKE SAME

BACKGROUND OF THE INVENTION

This application is a divisional of U.S. patent application Ser. No. 16/125,880, filed Sep. 10, 2018, which in turn claims the benefit under 35 U.S.C. § 119(e) of prior U.S. Provisional Patent Application No. 62/556,517, filed Sep. 11, 2017, which is incorporated in its entirety by reference herein.

The present invention relates to microporous membranes and to processes for producing microporous membranes and to hollow fiber and flat sheet membrane products, which incorporate the microporous membranes, and uses of these products.

Membranes which have selective permeabilities are widely used in various products, such as filtration media used in the medical field. Membranes having a form of hollow fiber are particularly suitable for the preparation of high area per volume membranes, such as hollow fiber membranes suitable for hemodialysis, hemofiltration, or hemodiafiltration. A variety of polymers, including polysulfone, polyethersulfone, cellulose, cellulose acetate, polyamides, polyacrylonitriles, polymethyl methacrylates, polyvinyl alcohols, polyolefins, and the like, have been used to form such hollow fiber membranes.

Water-soluble pore forming additives (e.g., polyvinylpyrrolidone (PVP), polyethylene glycol (PEG)) are generally added to membrane-forming polymers with hydrophobic characteristics (e.g., polysulfone (PSF), polyethersulfone (PES)) for fabrication of microporous membranes using a wet phase inversion process. These additives enhance the hydrophilicity and wettability of membranes for applications involving aqueous based fluids. In addition, water-soluble additives at the active surface of the membrane can enhance the membrane's anti-fouling behavior and blood compatibility during various applications such as kidney dialysis, blood oxygenation, and blood separation.

Water-soluble pore forming additives, however, can be leached out of the membrane core and the membrane's active surface during membrane fabrication as well as in membrane applications involving aqueous-based fluid. These applications can include, for instance, kidney dialysis, blood oxygenation, blood separation, water purification (or treatment), dairy processing, and separations in the biotechnology and pharmaceutical industry.

To balance the need for hydrolytic stability and other considerations, such as chemical and thermal resistances in membranes, the use of block copolymers comprising a hydrophilic block and a hydrophobic block can be used. Unlike additives such as polyvinyl pyrrolidone (PVP) or polyethylene glycol (PEG) that are added to the hydrophobic-base polymer as pore formers, the block copolymers comprise chemically bound structural units which can impart hydrophilicity, and are not as easily extracted during separation or cleaning operations. For instance, EP 1773913 B1 shows the use of polyarylethersulfone-polyalkylene glycol block copolymers in membrane fabrication. EP 2545096 B1 shows polyurethane block copolymers based on poly siloxane(tensides) with anchoring units, and their use as anti-bioadhesion additives in membrane preparation for microfiltration, ultrafiltration or gas separation or purification purposes.

As another approach, U.S. Patent Application Publication No. 2011/0263020 A1 shows a membrane which can be used for cultivating cells, wherein the membrane allows for the adhesion and proliferation of the cells based on its specific composition comprising polyurethane. U.S. 2011/0263020 shows certain hollow fiber membranes which have specific adhesive properties only on the outside, wherein the hollow fiber membranes can be prepared and used in applications which require adhesion and cultivation of cells exclusively on the inside or the outside, respectively. To provide this, U.S. 2011/0263020 states that the polyurethane additive is present only in the inside or outside layer of the membrane, supported by a separate layer not containing any polyurethane. U.S. 2011/0263020 suggests that such membranes can be prepared using a triple spinneret and two different polymer solutions, i.e., two different membrane layer forming solutions.

A need exists for improved strategies for incorporating additives with limited water solubility at the active surface of a membrane layer which can improve a membrane's hydrophilicity and wettability, improve membrane's anti-fouling behavior, improve membrane's blood compatibility, and/or maintain stable performance.

SUMMARY OF THE PRESENT INVENTION

A feature of the present invention is to provide a method for making a microporous membrane which meets the above and/or other needs.

A further feature of the present invention is to provide a microporous membrane that incorporates an additive of limited water solubility at the active surface of a membrane, which meets the above and/or other needs.

Additional features of the present invention are to provide products which incorporate the indicated microporous membrane and uses thereof.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method of making a microporous membrane that includes a) contacting polymer dope solution with precipitation fluid to precipitate the polymer dope solution to form a microporous membrane having a non-active region and at least one active surface, wherein the polymer dope solution comprises at least one polymer and at least one organic solvent, the precipitation fluid comprises at least one additive and a water-polar aprotic solvent mixture, wherein the additive itself has (i) low water solubility, (ii) hydrophilic properties, and (iii) solubility in the water-polar aprotic solvent mixture; b) rinsing the microporous membrane; and c) drying the rinsed microporous membrane; wherein at least a portion of the additive is delivered during at least one of a), b) and c) to at least one surface of the microporous membrane where the additive is coated, embedded, or both to provide an active surface of the microporous membrane containing the additive at a first composition in the active surface which is different from a second composition of the non-active region. The present invention further relates to microporous membrane products of the above-indicated method.

The present invention further relates to a microporous membrane comprising a non-active region and an active surface. The non-active region and the active surface each contain at least one polymer. The active surface contains at least one additive at a first composition in the active surface which is different from a second composition of the non-active region. The additive itself has (i) low water solubility, (ii) hydrophilic properties, and (iii) solubility in the water-polar aprotic solvent mixture.

The present invention further relates to a dialyzer or hemofilter comprising the above-indicated microporous membrane.

The present invention further relates to a process for at least one of membrane filtering or solute and/or solvent exchange comprising contacting aqueous-based fluid or blood with an above-indicated microporous membrane.

The present invention further relates to a process for dialysis, blood oxygenation, or blood separation filtering comprising contacting blood with an above-indicated microporous membrane. For purposes herein, the term "dialysis" can refer to any of the primary and secondary types of dialysis, which can include, e.g., hemodialysis (primary), peritoneal dialysis (primary), hemofiltration (primary), and/or hemodiafiltration (secondary).

It is to be understood that both the foregoing general description and the following detailed description are exemplary and explanatory only and intended to provide a further explanation of the present invention, as claimed.

BRIEF DESCRIPTION OF DRAWINGS

FIG. 4 is a process flow diagram of a method of production of a microporous hollow fiber membrane using wet spinning, according to an example of the present application.

FIG. 5 is a process flow diagram of a method of production of a microporous flat-sheet membrane, according to an example of the present application.

DETAILED DESCRIPTION OF THE PRESENT INVENTION

Figure 1:
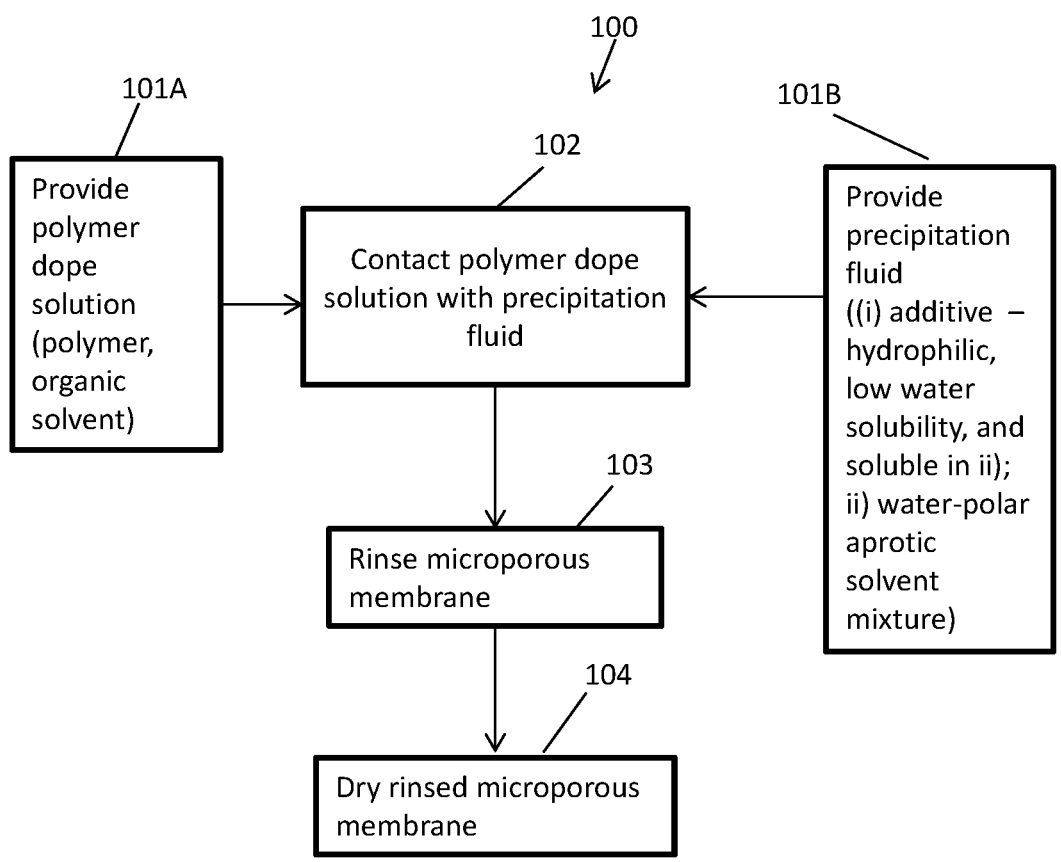
FIG. 1 is a process flow diagram of a method of production of a microporous membrane, according to an example of the present application.

Methods are disclosed for providing microporous membranes. The microporous membranes preferably have at least one hydrophilic polymer of limited water solubility incorporated as an additive at an active surface of the membrane. The incorporated additive at the membrane's active surface can improve one or more of the membrane's hydrophilicity, wettability, anti-fouling behavior, blood compatibility, and/or stability over long periods of use (e.g., 1 hour or more, 1 hour to 6 hours or more) or repetitive use (2 or 10 or 30 or more times). The additive can impart these beneficial effects without being vulnerable to excessive leaching out of the membrane layer that is modified with the additive. The method of the invention can provide such an improved membrane without need of a complicated production apparatus and while avoiding the need for post-membrane fabrication processing to provide limited water solubility at a membrane surface relative to the membrane core In the present invention, as an option, the at least one additive itself for the precipitation fluid has hydrophilic properties, limited water solubility, and solubility in the water-polar aprotic solvent mixture. As one option, the at least one additive (e.g., hydrophilic additive) for the precipitation fluid has limited water solubility of less than 10 wt % (0-10 wt %), or less than 5 wt %, or less than 1 wt %, or less than 0.1 wt %, in pure water at room temperature (20-23° C.), and is incorporated (e.g., coated, embedded, or both) at the active surface of a membrane from a precipitation fluid that contains a water-polar aprotic solvent mixture. As an option, the additive(s) can further have the property of being soluble in polar aprotic solvent.

For purposes herein, "an active surface" refers to the surface that comes into direct contact with the precipitation fluid that has the additive at the original composition of the precipitation fluid during the membrane fabrication step. The active surface can comprise the surface region of the membrane where the additive is present. Additive can also be present in the non-active region of the membrane, but in lower concentrations compared to the active surface. The non-active region is defined as the region of the membrane that does not come in direct contact with the starting precipitation fluid that has the additive during the membrane fabrication step. However, it is to be understood that the non-active region(s) can be exposed to the precipitation fluid at some stage of the fabrication wherein the make-up of the precipitation fluid may change (e.g., higher content of water). The non-active region of the membrane can be the non-active surface or the core of the membrane or both. As used herein, the term "core" or "core region" can refer to an inner geometrical center of the membrane body.

In making the microporous membrane, the precipitation fluid, including the indicated additive, is brought into contact with a polymer dope solution before the membrane is formed. Membrane formation is initiated upon contact being made between the precipitation fluid and the polymer dope solution. The polymer dope solution can comprise a membrane-forming polymer or polymers and at least one organic solvent in solution. As an option, additives with limited water solubility can be added to the membrane's active surface during the fabrication step to mitigate or control dissolving the additive with limited water solubility into the precipitation fluid. The precipitation fluid is used to coagulate the polymer dope solution.

The precipitation fluid which can be used in the present invention is a mixture of water and a polar aprotic solvent in which the water acts as a non-solvent and precipitates the polymer dope solution into a microporous membrane. The additive itself with limited water solubility is soluble in the precipitation mixture in an amount needed to make membranes with desirable properties, or can be modified (e.g., protonated) to dissolve in the precipitation mixture in an amount needed to make membranes with desirable properties. Since leaching during fabrication and application is a concern, the additive is preferably selected to be a material that has limited solubility in water at temperatures of fabrication or end use. The additive which has limited solubility in water is soluble in and can be dissolved in the polar aprotic solvent and the water-polar aprotic solvent mixture. The polymer dope solution can be extruded in tubular form (e.g., hollow fiber), such as by wet spinning, or cast in flat film form, or formed into other shapes which have a surface that is contactable with the precipitation fluid. The contacting of the polymer dope solution with the precipitation fluid causes coagulating of the polymer dope solution from which a solidified membrane with active membrane surface can be formed. The extrudate, cast film, or other membrane formed can then be rinsed and dried. The solidified membrane can have increased wettability, such as compared to a membrane formed using a precipitation fluid without the additive that has limited water solubility.

The resulting microporous membrane can have a varying composition of the additive with limited water solubility at the membrane's active surface relative to other membrane regions, e.g., non-active regions. The additive, as an option, can be present in the microporous membrane in a gradient. The additive can be present in the membrane in a concentration profile, as an option, wherein the concentration of additive can be greater or highest at the active membrane surface and then decrease (linearly or non-linearly (e.g., exponential and sigmoidal)) in a direction from the membrane active surface towards the non-active regions. The ratio of the active surface region thickness to the total thickness of the membrane can be, as an option, from about 1:2.5 to about 1:5, or from about 1:2 to about 1:4.5, or from about 1:1.5 to about 1:4, or other ratio values. The distribution of additive in the membrane can be analyzed and determined using Raman spectroscopy, XPS elemental analysis, energy dispersive X-ray spectroscopy (EDS or EDX), or other suitable analytical technique for this evaluation. The extent of coating and/or embedding of the additive from the active surface of the membrane which was contacted with the precipitation fluid into the bulk of the membrane diffuses towards the non-active regions that were not directly contacted with the precipitation fluid, can be analyzed in this manner. As an option, the active surface of the membrane can have a composition which contains a higher volumetric concentration of the additive compared to the composition of the core or core region, or a non-active surface, or both. As an option, the active surface of the membrane can contain a concentration of the additive which is at least about 10 vol. % higher, or at least about 20 vol % higher, or at least about 30 vol % higher, or at least about 40 vol % higher, or at least about 50 vol % higher, or at least about 60 vol % higher, or at least about 70 vol % higher, or at least about 80 vol % higher, or at least about 90 vol % higher, or from about 10 vol % higher to all the additive content, or from 15 vol % to about 99 vol % higher, or from about 20 vol % to about 80 vol % higher, or other higher concentrations, compared to the composition of the core or core region of the membrane, or non-active region, or the non-active surface, or both.

As an option, considering all of the additive in the microporous membrane, at least about 10 wt. %, or at least about 20 wt %, or at least about 30 wt %, or at least about 40 wt %, or at least about 50 wt %, or at least about 60 wt %, or at least about 70 wt %, or at least about 80 wt %, or at least about 90 wt %, or from about 10 wt % to about 99 wt %, or from 15 wt % to about 90 wt %, or from about 20 wt % to about 80 wt %, or from about 30 wt % to about 70 wt %, or other percentage amounts, of all the additive in the microporous membrane can be present in the active surface As an option, the active surface can have a higher gravimetric density compared to density of the core or non-active surface, or both, such as at least about 5% higher, or at least about 10% higher, or at least about 20% higher, or at least about 25% higher, from 5% to 50% higher or other values. As an option, considering all of the additive in the microporous membrane, the additive can be present in the membrane in an amount of at least about 0.1 wt. %, or at least about 0.25 wt %, or at least about wt %, or at least about 0.75 wt %, or at least about 1 wt %, or at least about 1.25 wt %, or at least about 1.50 wt %, or at least about 2 wt %, or at least about 2.5 wt %, or at least about 3 wt % or 4 wt % or 5 wt % or 6 wt % or 7 wt % or 8 wt % or 9 wt %, or from about 0.1 wt % to about 10 wt %, or from wt % to about 9 wt %, or from about 0.5 wt % to about 8 wt %, or from about 0.75 wt % to about 7 wt %, or from about 1 wt % to about 6 wt %, or from about 1.25 wt % to about 5 wt %, or other percentage amounts, based on total weight of the microporous membrane.

In an option, the membrane polymer and additive can be contained in a same region or single layer of the microporous membrane. In another option, 100% of the additive can be used as a coating on the active surface of the membrane. This preferred membrane structure can be formed, as an option, by wet spinning or casting a polymer dope solution that is free, or essentially free (e.g., <0.1 wt %), of the additive and directly contacting the polymer dope solution with a precipitation fluid that includes the additive having limited water solubility. The precipitation fluid itself, as a preferred option, is not formulated to be formable into a self-supporting membrane structure, whereas the polymer dope solution is membrane-formable, i.e., the polymer dope solution is formable into polymeric matrix defining a self-supporting membrane structure.

In an option, the present invention relates to a method of making a microporous membrane which comprises steps of a) contacting a polymer dope solution with a precipitation fluid to precipitate the polymer dope solution to form a microporous membrane having a core and at least one surface, b) rinsing the microporous membrane, and c) drying the rinsed microporous membrane. In this process, the polymer dope solution comprises at least one polymer and at least one organic solvent, and the precipitation fluid comprises additive and water-polar aprotic solvent mixture. As an option, the additive has (i) low water solubility, (ii) hydrophilic properties, and (iii) solubility in the water-polar aprotic solvent mixture. At least a portion of the additive is delivered during at least one of steps a), b) and c) to the at least one surface of the microporous membrane where the additive is coated, embedded, or both to provide an active surface of the microporous membrane containing the additive at a first composition in the active surface which is different from a second composition of the core. The additive can be delivered during step a). The additive can be delivered during step b). The additive can be delivered during step c).

The polymer dope solution can be provided by dissolving at least one membrane-forming polymer in at least one organic solvent to form the polymer dope solution, and the additive can be dissolved in a water-polar aprotic solvent mixture to provide the precipitation fluid. The polymer dope solution and precipitation fluid each can be prepared concurrently with performing the other steps a), b), and c) for producing the microporous membrane, or each can be prepared or obtained in advance of performing the other steps and stored until used in producing the microporous membrane. The polymer dope solution and precipitation fluid each can be prepared on-site, or prepared off-site, or obtained from a different source located off-site, relative to the location(s) where one or more of the other steps a), b) and c) of the method are performed. As an option, the preparation of the polymer dope solution and precipitation fluid is done as part of a production line that is integrated with steps a), b), and c).

The additive having limited water solubility can be a solid at about 25° C., such as a solid form that is dissolvable in the precipitation fluid. The solid form of the additive may be a solid particulate (e.g., powder, pellets, or other flowable dry solid particles), or a solid thin film. The additive can have a solubility in the water-polar aprotic solvent mixture of the precipitation fluid of from about 100 ppm to about 5,000 ppm, or from about 150 ppm to about 4,000 ppm, or from about 250 ppm to about 3,000 ppm, or from about 500 ppm to about 2,000 ppm, or from about 750 ppm to about 1,500 ppm, or other values. The additive, as an option, can be a pore-forming material in the microporous membrane. During the solvent exchange process of the membrane formation, the additive can get re-distributed throughout the membrane, but with much higher concentration on the side that is in direct contact with the additive solution. The additive leaching, as an option, can be less than about 40 wt %, or less than about 35 wt %, or less than about 30 wt %, or less than about 25 wt %, or less than about 20 wt %, or less than about 15 wt %, or less than about 10 wt %, or less than about 5 wt %, or from 0 wt % to about 40 wt %, or from about 1 wt % to about 35 wt %, or from about 2 wt % to about 30 wt %, or from about 3 wt % to about 25 wt %, or from about 4 wt % to about 20 wt %, or from about 5 wt % to about 15 wt %, based on the wt % of additive delivered to the membrane from the precipitation fluid. A polymer material can be selected for the additive which provides these properties.

The additive having limited water solubility that is added to the precipitation fluid, as an option, can be a nitrogen-containing polymer which has at least one oxygen-containing moiety. The additive, as an option, can be polyurethane, chitosan, or other N-containing polymers having an oxygen containing moiety (e.g., a hydroxyl group(s), carbonyl, oxygen chain linkage, or others), or any combinations thereof.

Polyurethanes which can be suitable for the membrane-forming method and membrane products thereof of the present invention can be identified by their dissolvability and solubility in the water-polar aprotic solvent mixtures used in membrane formation at the desired water composition range. Polyurethanes which contain a high composition of hydrophilic segments, as an option, which allow the additive to be soluble in a water-polar aprotic solvent mixture at the desired water composition but has limited solubility in water, can be used. A hydrogel grade of polyurethane, as an option, also can be suitable in this respect. Besides the composition and characteristics of the hydrophilic segments, other properties of polyurethanes, such as molecular weight, and degree of crosslinking and chain extenders, can influence their solubility in water-solvent mixtures, and can be taken into account in selecting the polyurethane.

As an option, the additive can be a hydrogel or be a hydrogel grade material (e.g. polymer).

As an option, the additive may absorb water ranging from 20 to 1000% of its dry weight at equilibrium, such as from 20 to 60%, or from 20 to 100%, or from 20 to 150%, or from 20 to 500%, or from 20 to 900%, or from 60 to 100%, or from 60 to 150%, or from 60 to 500%, or from to 900%, or from 60 to 1000%, or from 100 to 150% or from 100 to 900%, or from 100 to 1000%, or from 500 to 900%, or from 500 to 1000%, or even greater than 1000%.

The additive, as an option, can be a hydrophilic aliphatic thermoplastic polyurethane. The additive, as an option, can be a hydrogel grade of polyurethane, such as an aliphatic polyether based hydrogel thermoplastic polyurethane. Examples of commercially available hydrophilic aliphatic polyether polyurethanes which can be used include, e.g., the TECOPHILIC® grades of polyurethanes, which are manufactured by Lubrizol LifeScience Polymers. The TECOPHILIC® brand of products are hydrophilic aliphatic polyether urethanes. These TECOPHILIC® products may absorb water ranging from 20 to 1000% of their dry weight at equilibrium, such as from 20 to 60%, or from 20 to 100%, or from 20 to 150%, or from 20 to 500%, or from 20 to 900%, or from 60 to 100%, or from 60 to 150%, or from 60 to 500%, or from 60 to 900%, or from 60 to 1000%, or from 100 to 150% or from 100 to 900%, or from 100 to 1000%, or from 500 to 900%, or from 500 to 1000%, or even greater than 1000% in some grades. TG-500 and TG-2000 are TECOPHILIC® polyurethanes, for example, which can be used as the additive in the present invention. Additional information on these polymers is provided in the examples.

The additives, such as when commercially obtained, may be pre-combined with smaller amounts of other co-additives, such as antioxidants, UV stabilizers, antiozonates, antifoams, plasticizers, processing aids, stearates, dyes, and/or colorants, and so forth, which can be tolerated in the membrane compositions of the present invention.

The additive included in the precipitation fluid, as an option, can be chitosan. As an option, the chitosan can be protonated before introduction into the water-polar aprotic solvent mixture to make precipitation fluid. As an option, the chitosan can be protonated in the presence of weak acid (e.g., $K_a$ of weak acids varies between $1.8 \times 10^{-16}$ and 55.5) and then added to water-polar aprotic solvent mixture to make a precipitation fluid before contacting a polymer dope solution. Chitosan has the ability to protonate in the presence of weak acid (e.g., acetic acid ($K_a$ is $1.76 \times 10^{-5}$), formic acid ($K_a$ is $1.77 \times 10^{-4}$)). This is desirable for an additive like chitosan since it can form a protonated form of chitosan that is soluble in a mixture of water and polar aprotic solvent used in the precipitation fluid, and can be incorporated at least into an active surface of a membrane from contacting a polymer dope solution with the precipitation fluid. Chitosan can have the structure shown in Figure (I):

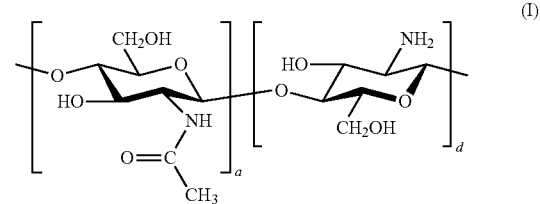

The chitosan units in structure (I) are present in ("d") number of units and chitin units may be present in ("a") number of units. A starting chitosan may be mainly or completely composed of chitosan units with only some or no chitin units. As an option, the chitosan may be protonated in situ in a precipitation fluid in the co-presence of weak acid and a mixture of water and polar aprotic solvent. A preferred method to prepare the precipitation mixture is to first add chitosan and weak acid to water in order to dissolve chitosan and then add polar aprotic solvent or water-polar aprotic solvent mixture. The degree of protonation of the chitosan in the precipitation fluid before it contacts a polymer dope solution preferably is essentially complete (e.g., at least 98 wt %) or complete (100%) in the precipitation fluid before contacted to a polymer dope solution. The protonation of chitosan converts the amino group (—$NH_2$) in the chitosan unit to a —$NH_3^+$ group. While not desiring to be bound to a particular theory, upon membrane formation using a precipitation fluid that contains protonated chitosan, the $NH_3^+$ group in chitosan units may revert to the amino group ($—NH_2$) form as the weak acid gets rinsed out of the membrane. Based on this, the additive present in the membrane product can be chitosan.

As an option, a compound that can protonate chitosan can be a weak acid (e.g., acetic acid, acetic acid anhydride, lactic acid, formic acid or a combination of acids, their anhydrides, or both), which can protonate the amines of chitosan molecule to provide protonated chitosan that is soluble in the mixture of water and polar aprotic solvent used in the precipitation fluid. As a preferred option, the weak acid is a weak organic acid or anhydride thereof, or both. The relative amounts of weak acid and chitosan used in the preparation of the precipitation fluid for this purpose can be sufficient to support the protonation of the amine groups of chitosan and degree of protonation needed. As an option, the protonated chitosan can be incorporated into the precipitation fluid with mixing and without the need for the weak acid being present in the precipitation fluid for protonation of chitosan.

The polar aprotic solvent of the water-polar aprotic solvent mixture of the precipitation fluid can be, as an option, at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), or butyrolactone, or any combination thereof.

The precipitation fluid also contains an inorganic solvent, such as water, in a sufficient amount in order to make possible precipitation of the polymer dope solution to the desired degree. In a preferred option, the inorganic solvent is water. As an option, sufficient water is included in the precipitation fluid such that the contacting of the precipitation fluid with the polymer dope solution can initiate coagulation in the formation of the membrane. As an option, the precipitation fluid contains at least about 25 wt % water, or at least about 30 wt % water, or from about 25 wt % to about 75 wt % water, or from about 30 wt % to about 70 wt % water, or other amounts, based on total weight of the precipitation fluid. The remainder of the precipitation fluid can be comprised of the polar aprotic solvent and the additive, and any weak acid included (e.g., in the case of chitosan additive).

The precipitation fluid can have a composition, as an option, of from 75 wt % to about 25 wt % polar aprotic solvent and from about 75 wt % to about 25 wt % water, based on total weight of the precipitation fluid, and at least about 100 ppm (e.g., from about 100 ppm to about 5,000 ppm) additive based on concentration in the water-polar aprotic solvent mixture of the precipitation fluid. In another option, the precipitation fluid comprises a composition of from about 70 wt % to about 30 wt % polar aprotic solvent and from about 70 wt % to about 30 wt % water, based on total weight of the precipitation fluid, and from about 100 ppm to about 4,000 ppm additive based on concentration in the water-polar aprotic solvent mixture of the precipitation fluid. If chitosan is used as an additive that is protonated, the precipitation fluid can have a composition, as an option, of from about 75 wt % to about 25 wt % polar aprotic solvent, from about 75 wt % to about 25 wt % water, and from about 0.01 wt % to about 0.5 wt % weak acid, based on total weight of the precipitation fluid, and at least about 100 ppm (e.g., from about 100 ppm to about 5,000 ppm) additive (e.g., based on added chitosan or protonated chitosan formed therefrom that is present in the precipitation fluid) or other amounts of the additive indicated herein, based on concentration in the water-polar aprotic solvent mixture of the precipitation fluid. As an option, the amount of acid used for protonation can be about 1:1 by weight with respect to chitosan. Other compositions of the precipitation fluid solution which include these components may be used.

The polymer dope solution can comprise a mixture of at least one polymer (e.g., at least one membrane-forming polymer) and at least one organic solvent that can dissolve the polymer. The mixture of polymer and organic solvent, as a preferred option, can be a homogenous mixture.

The membrane-forming polymer, in an option, is a hydrophobic polymer. The membrane-forming polymer can be, as an option, at least one of polysulfone (PSF), polyethersulfone (PES), polyarylsulfone (PAS), polyarylethersulfone (PAES), polyvinylidene fluoride (PVDF), polyacrylonitrile (PAN), or any copolymer thereof. The membrane-forming polymer, such as when commercially obtained, may be pre-combined with smaller amounts of other co-additives, such as those indicated for the additive having limited water solubility that is added to the precipitation fluid, which can be tolerated in the membrane compositions of the present invention.

The organic solvent used to dissolve the membrane-forming polymer can be, as an option, at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), or butyrolactone. As a preferred option, the organic solvent used to dissolve the membrane-forming polymer is a polar aprotic solvent. The organic solvent can dissolve the membrane-forming polymer(s) used for making the microporous membrane, e.g., by wet phase inversion process.

The polymer dope solution, as an option, can further comprise at least one hydrophilic polymer, such as polyvinylpyrrolidone (PVP) or polyethylene glycol (PEG), or other hydrophilic polymers. If included, the amount of any hydrophilic polymer included in the polymer dope solution can be limited to amounts that do not cause a leaching problem. The hydrophilic polymer, if used in the polymer dope solution, as an option, is a polymer other than polyurethane or chitosan. Though polyurethane may be included in the polymer dope solution, as an option, it is not required. Without wishing to be bound to a particular theory, the presence of the indicated additive having limited water solubility may be quite useful in the precipitation fluid to provide a membrane with an active surface having limited water solubility, wettability, and other advantageous properties indicated herein.

The polymer dope solution can have limited or no water content. Premature coagulation of the polymer dope solution is undesirable to an extent that it would interfere with the ability of the polymer dope solution to extrude or cast or otherwise shape the polymer dope solution into a desired form of the membrane for contact with the precipitation fluid and/or to interact in the desired manner with the precipitation fluid. Water content of the polymer dope solution can be, as an option, less than about 7 wt % water, e.g., 0-6.9 wt % water, or 0-6 wt % or water, or 0-5 wt % water, or 0-4 wt % water, or 0-3 wt % water, or 0-2 wt % water, or 0-1 wt % water, or other amounts, based on total weight of the polymer dope solution.

The polymer dope solution can have a composition, as an option, of from about 12 wt % to about 30 wt % membrane-forming polymer, from about 88 wt % to about 63 wt % organic solvent (e.g., polar aprotic solvent), and less than about 7 wt % water, based on total weight of the polymer dope solution. In another option, the polymer dope solution can have a composition of from about 13 wt % to about 19 wt % polymer, from about 87 wt % to about 75 wt % polar aprotic solvent, and less than about 6 wt % water, based on total weight of the polymer dope solution. Other compositions of the polymer dope solution which include these components may be used.

The resulting combination of components in the polymer dope solution can be mixed, filtered, and spun into hollow fibers, or cast into a film, with contact made with the precipitation fluid and further processed to form a microporous membrane.

Referring to FIG. 1, a method of forming a microporous membrane according to an example of the present application, indicated by the identifier 100, includes steps 101A, 101B, 102, 103, and 104. In steps 101A and 101B, polymer dope solution and precipitation fluid are provided, which are used in the production of the microporous membrane. The contacting of the polymer dope solution with precipitation fluid in step 102, is followed by rinsing of the membrane in step 103 and drying the rinsed membrane in step 104.

Figure 2:
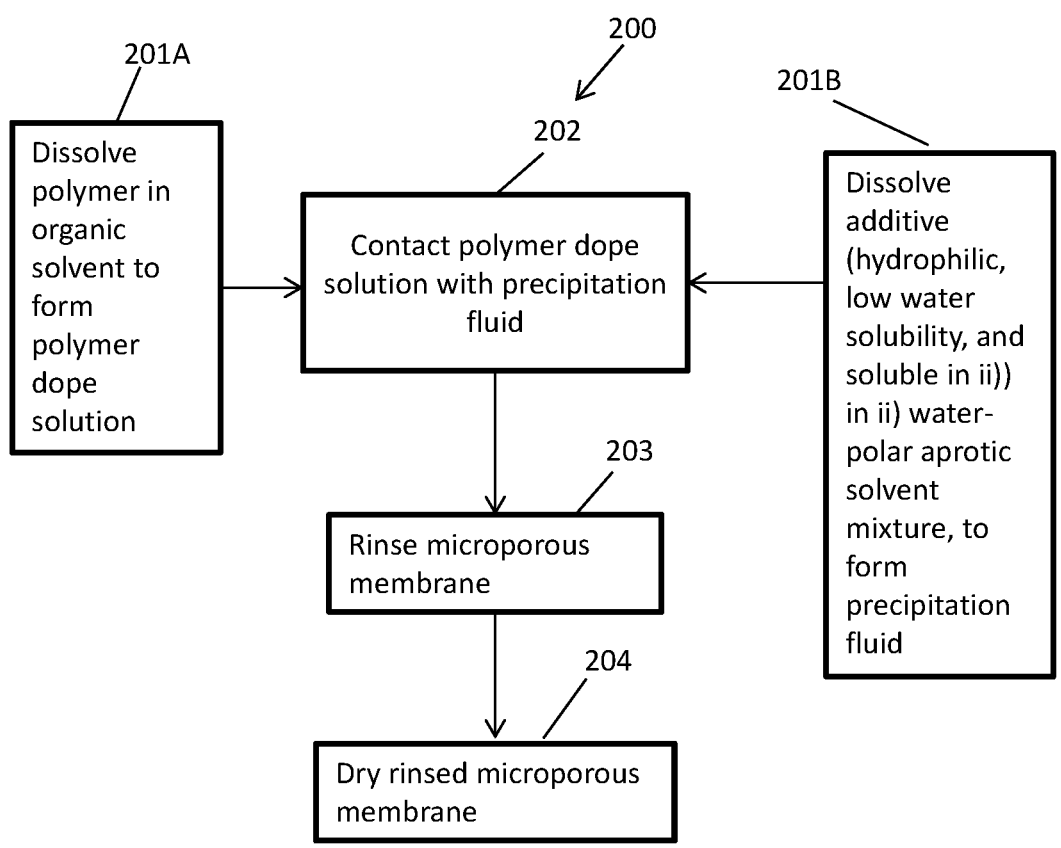
FIG. 2 is a process flow diagram of a method of production of a microporous membrane, according to an example of the present application.

Referring to FIG. 2, a method of forming a microporous membrane according to an example of the present application, indicated by the identifier 200, includes steps 201A, 201B, 202, 203, and 204. In step 201A, the polymer dope solution is formed by dissolving the membrane-forming polymer in organic solvent. In step 201B, precipitation fluid is provided from dissolving the additive in the water-polar aprotic solvent mixture. The contacting of the polymer dope solution with precipitation fluid in step 202, is followed by rinsing of the membrane in step 203 and drying the rinsed membrane in step 204.

Figure 3:
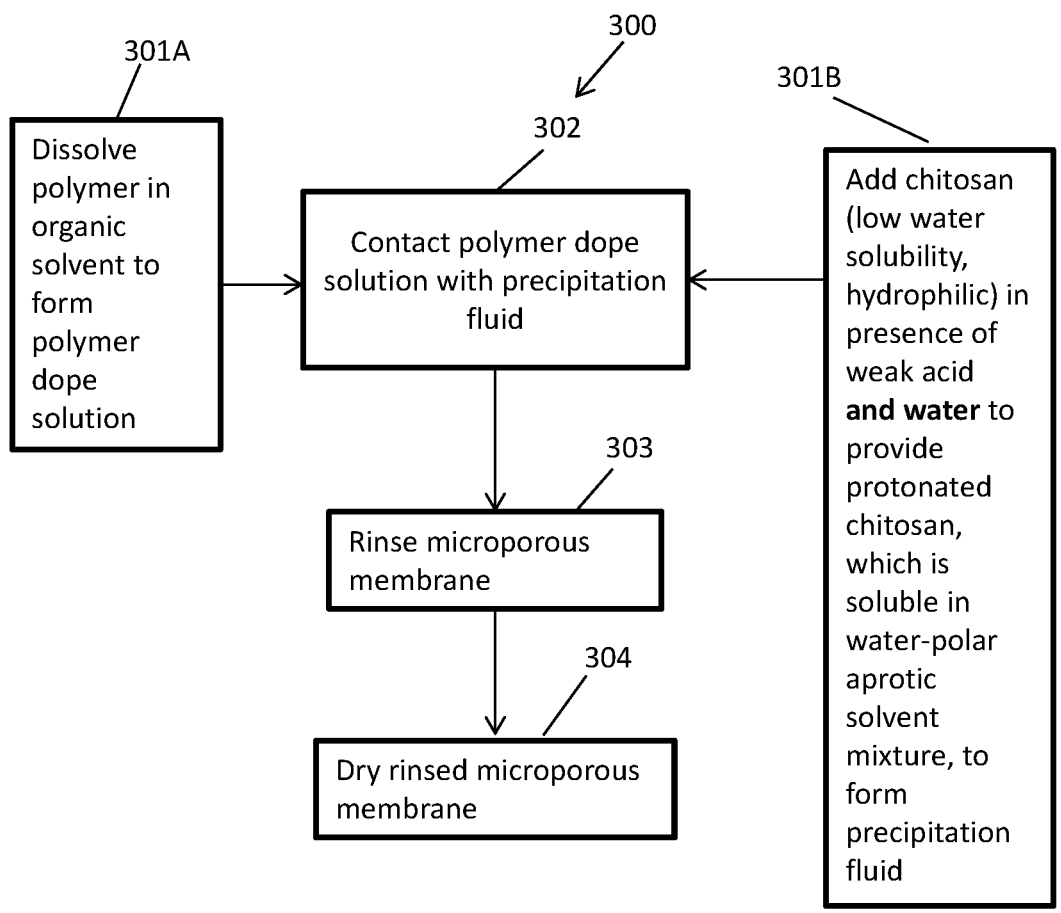
FIG. 3 is a process flow diagram of a method of production of a microporous membrane which includes a step of modifying (e.g. protonating) an additive in situ in the precipitation fluid, according to an example of the present application.

Referring to FIG. 3, a method of forming a microporous membrane using chitosan additive according to an example of the present application, indicated by the identifier 300, includes steps 301A, 301B, 302, 303, and 304. In step 301A, like step 201A of FIG. 2, the polymer dope solution is formed by dissolving the membrane-forming polymer in organic solvent. In step 301B, the precipitation fluid is provided from a multi-stage procedure wherein chitosan is protonated by the presence of a weak acid and water, which forms a protonated chitosan that can dissolve in the water-polar aprotic solvent mixture that also is present. The contacting of the polymer dope solution with resulting precipitation fluid in step 302, is followed by rinsing of the membrane in step 303 and drying the rinsed membrane in step 304. As indicated, the protonated group in the chitosan can revert to the original amino form in the fabrication of membrane, such that chitosan is the additive present in the membrane product.

Following drying of the rinsed membrane (for instance as in step 304 above), and prior to use, the membrane may be primed (e.g. in saline or other acceptable fluid) for a standard or prolonged period to rehydrate the membrane and any associated additive, such as for example, to a predetermined moisture content, or for a predetermined time. For purposes of the present invention, a standard priming with saline or other fluid may generally last 10 minutes or about 10 minutes. Further, a prolonged period of priming with saline or other fluid may be 16 hours or about 16 hours. The priming procedure is described below. Other priming times can be used greater than or less than the times mentioned here. The longer or prolonged period of priming permits a more full rehydration of the additive that is part of the membrane and optionally results in the rehydration of other parts of the membrane.

For example, dialyzers were primed by filling and recirculating saline on the blood side of the dialyzer for 10 minutes and filling the dialysate side with saline without circulation (standard in vitro test priming). For prolonged priming, after the 10 minute recirculation, the recirculating saline was stopped and the blood and dialysate ports of the dialyzer were capped. The dialyzer then remained closed for an additional 16 hours in the incubator at 37° C. with the blood and dialysate sides completely filled with saline.

Without wishing to be bound to a particular theory, prolonged priming of the dialyzers may facilitate water absorption by the additive in the dialyzer, optionally enhancing the hemocompatibility of the membrane's active surface. It is understood that saturation of the additive with water/fluid is a time-dependent process that is influenced by a variety of other factors (e.g., temperature, nearby polar/nonpolar groups, exposure on the surface of the membrane, etc.), and reflects a state of chemical equilibrium in water/fluid transfer between the additive and its surrounding bath. Prolonged priming is expected to increase saturation of the additive/membrane to achieve this equilibrium. Partial or complete saturation of the additive in the membrane with water may thus be associated with improved hemocompatibility. In like manner, this saturation may also be described in terms of "wetting" of the membrane, with complete wetting of the membrane associated with a fully saturated additive, for example. This improved hemocompatibility, such as may be measured by reduced platelet reduction, may also be seen with only somewhat prolonged priming periods, as may increase saturation of the additive, in a dose (e.g., time)-dependent manner.

Optionally, the need for prolonged priming may be minimized or eliminated by employing an additive with enhanced water absorption properties and/or enhancing the availability of additive in the membrane matrix for water absorption. For example, additives with smaller molecular weight and/or a higher degree of hydrophobicity can be used to minimize or eliminate the need for prolonged priming in order to saturate the additive with water.

In addition, while the additive may be the primary water-absorptive element of the microporous membrane, saturation may generally be described in terms of the overall membrane. Thus, a saturated microporous membrane may be expected to contain a saturated additive in some cases, assuming equilibrium between the additive and surrounding milieu.

In some embodiments, a microporous membrane containing the additive can have a lower blood platelet reduction relative to a microporous membrane without the additive but otherwise is the same. The microporous membrane containing the additive can have at least a 30% lower, a 40% lower, a 50% lower, a 60% lower, a 70% lower, an 80% lower, a 90% lower, or a 95% lower blood platelet reduction relative to the microporous membrane without the additive (e.g., 30% to 95% lower blood platelet reduction relative to the microporous membrane without the additive).

As an option, prolonged priming (or saturation) of a microporous membrane containing the additive can be associated with a lower blood platelet reduction relative to the microporous membrane containing the additive following a shortened or a standard priming period. The microporous membrane containing the additive following a prolonged priming period (or full saturation) can be at least 10% lower, at least 20% lower, at least 30% lower, at least 40% lower, or even at least 50% lower blood platelet reduction relative to the same microporous membrane containing the additive but following only a shortened or a standard priming period.

In the present invention, it has been discovered that a membrane subjected to a prolonged period of priming results in a lower percent platelet reduction (an improvement) compared to the same membrane that was primed using the standard period. By priming the microporous membrane of the present invention using the prolonged period, this results in a more consistent platelet reduction property and/or other desirable membrane or dialysis properties and/or further optionally results in a more predictable platelet reduction.

In the present invention, as an option, the standard deviation for percent platelet reduction using the microporous membrane of the present invention can be 50% or less of the average percent platelet reduction when primed for 10 minutes and can be 10% or less of the average percent platelet reduction when primed for 16 hours. As an example, this standard deviation for percent platelet reduction of a microporous membrane of the present invention can be 45% or less, 40% or less, such as from 25% to 50% of the average percent platelet reduction, when primed for 10 minutes and the standard deviation can be 10% or less, 8% or less, 5% or less, or from about 2% to about 10% of the average percent platelet reduction when primed for 16 hours.

In the present invention, a microporous membrane of the present invention can have a standard deviation with respect to percent platelet reduction of below 5, or below 2, such as a standard deviation of 3, 4, 5, or 6 based on at least three samples that are tested and preferably based on three samples. This standard deviation is preferred when the percent platelet reduction is determined for a microporous membrane that has been primed for 16 hours as described herein.

Further, the standard deviation of the percent platelet reduction of a standard primed microporous membrane compared to a prolonged primed microporous membrane can have a standard deviation ratio of from about 0.5:15 to about 2:9 or 1:12 to 1:9 (prolonged priming: standard priming).

As indicated, the microporous membrane that can be produced by a method of the present invention can have a shape of a hollow fiber, or a flat sheet membrane, or other self-supporting shapes.

Where the microporous membrane is a hollow fiber, a hollow fiber can be produced in a method of the present invention, as an option, which comprises extruding or wet spinning the polymer dope solution through an outer ring duct of a spinneret comprising the outer ring duct and an internal hollow core, and simultaneously, passing the precipitation fluid through the internal hollow core, wherein the precipitation fluid acts directly on the polymer dope solution after issuing from the spinneret. The spun fiber can be cast into an aqueous washing bath with an air gap provided between the spinneret and aqueous washing bath. Precipitation of dope solution can initiate as the precipitation fluid comes into contact with the precipitation fluid. The precipitation process can continue into an aqueous washing bath. After precipitation, the coagulated fiber can be rinsed in a bath that can contain water and in which the hollow fiber can be temporarily held for washing out dissolved organic liquid constituents and for fixing the microporous structure of the fiber. After that, the fiber can be passed through a hot drying zone. The hollow fiber optionally can be texturized in order to improve the exchange properties thereof After this, the fiber so produced can be handled in conventional manners, for example, by winding onto a bobbin, cutting the fibers to a desired length, bundled, and/or used in manufacture of dialyzers from the cut fiber in conventional manners.

Referring to FIG. 4, a method according to an example of the present application for producing a hollow fiber membrane, indicated by the identifier 400, includes steps 401, 402, and 403. As indicated, in step 401, polymer dope solution can be extruded through spinneret outer ring duct. In step 402, simultaneously with 401, precipitation fluid passes through the spinneret internal hollow core. The precipitation fluid directly contacts the inner surface of the polymer dope solution discharged from the spinneret. In step(s) 403, the hollow fiber is rinsed and dried. A substantial portion of the solvents can be dissolved and washed out of the fibers formed, and the fibers can be collected, dried, and cut to desired lengths. To implement the wet spinning method, as an option, the spinneret can be configured to extrude a single polymer dope solution through a single outer ring duct relative to the spinneret hollow core through which the precipitation fluid passes. Though available as an option, it is not necessary to extrude multiple polymer dope solutions to form multiple-layered membranes. As indicated, the precipitation fluid provides a source of the additive that is incorporated into an active surface of the membrane layer.

A wet-spinning spinneret which can be used for spinning hollow fibers of the present invention can be types, for example, shown in U.S. Pat. Nos. 3,691,068; 4,906,375; and 4,051,300, all of which are incorporated in their entireties by reference herein. The indicated polymer dope solution containing the fiber forming polymer and organic solvent can be pumped to an annular extrusion spinneret having concentric tubes. The spinneret or nozzle, for example, can have a ring duct with a diameter equaling or approximating the desired outer diameter of the hollow fiber. For example, as wet spinning dimensions, the outer diameter orifice can be, as an option, from about 0.2 mm to 0.5 mm and the inner diameter can be from about 0.1 mm to about 0.4 mm, or other suitable sizes. A spinneret hollow core can typically extrude solution coaxially into and through this duct through which the precipitating fluid is fed simultaneously with polymer dope solution being fed between the outer surface of the hollow core and inner bore of the ring duct. The precipitating fluid can be pumped through this hollow core so that the precipitating solution emerges from the core tip and makes contact with the hollow fiber configuration that is made up of the extruded polymer dope solution. As indicated, a hollow fiber or capillary membrane can be formed by the precipitating fluid acting in an outward direction on the polymer solution after issuing from the wet-spinning spinneret.

The amount or ratio of the precipitating fluid supplied to the polymer dope solution in the spinneret can be dependent, for example, on the dimensions of the wet-spinning spinneret, that is to say, the dimensions of the finished hollow fiber. In this respect, it can be desirable, as an option, that the dimensions of the fiber upon precipitation are not changed from those of the hollow fiber configuration before precipitation but after extrusion. As an option, the amount of first composition of the active surface can be controlled by controlling the ratio of the precipitating fluid to the polymer dope solution. The ratios of the volumes used of precipitating fluid to polymer dope solution can be in a range, as an option, of from about 1:0.5 to about 1:4, or other values, given an equal flow rate of the precipitating fluid and of the polymer dope solution, to the area ratios of the hollow fiber, i.e. the ring-area formed by the polymeric substance and the area of the fiber lumen. The precipitating fluid can be supplied to the extruded configuration directly upstream from the spinneret such that the inner or lumen diameter of the extruded and not yet precipitated configuration generally corresponds to the dimensions of the ring spinneret, from which the material is extruded. It can be useful if the outer diameter of the hollow fibers, as an option, is equal to from about 0.1 mm to about 0.5 mm, whereas the thickness of the membrane can be from about 10 µm to 100 µm or from about 15 µm to 50 µm.

As indicated, the present invention can be applied to fabrication of flat sheet membranes. The polymer dope solution containing the membrane-forming polymer and solvent can be coated and solidified in place as a continuous or discontinuous coating or film on a substrate surface (e.g., woven or non-woven). However, standard flat sheet casting procedures, such as described in U.S. Pat. No. 3,615,024, are not designed to fabricate a flat sheet membrane with active surface having higher concentration of the additive than the core according to the present invention. A method and apparatus of the present invention is used to produce a flat sheet microporous membrane with an active surface having higher concentration of the additive than the core can be fabricated.

In a method of the present invention for making a flat sheet membrane, as an option, the polymer dope solution can be cast onto a surface of a carrier using a doctor blade or knife to provide a film-coated carrier, wherein the film is the polymer dope solution, and at least a portion of the precipitation fluid which comprises the additive and water-polar aprotic solvent mixture can be cast onto a surface of the film-coated carrier using a doctor blade or knife, wherein the precipitation fluid acts directly on the polymer dope solution in the film to provide a surface-treated film-coated carrier. Then, the surface-treated film-coated carrier can be conveyed through a precipitation bath containing a precipitation fluid and further processed as needed to provide a microporous membrane containing product.

Referring to FIG. 5, a method of production of a microporous flat-sheet membrane according to an example of the present invention, indicated by the identifier 500, includes steps 501, 502, 503, and 504. As indicated, in step 501, polymer dope solution is cast onto the carrier surface using a doctor blade/knife to form a film-coated carrier; in step 502, precipitation fluid is cast onto the surface of the dope solution film-coated carrier using a doctor blade/knife to form a precipitation fluid surface-treated dope solution film-coated carrier; in step 503, the surface-treated film-coated carrier is conveyed through a precipitation bath; and step 504, the microporous membrane is rinsed and dried.

Figure 6:
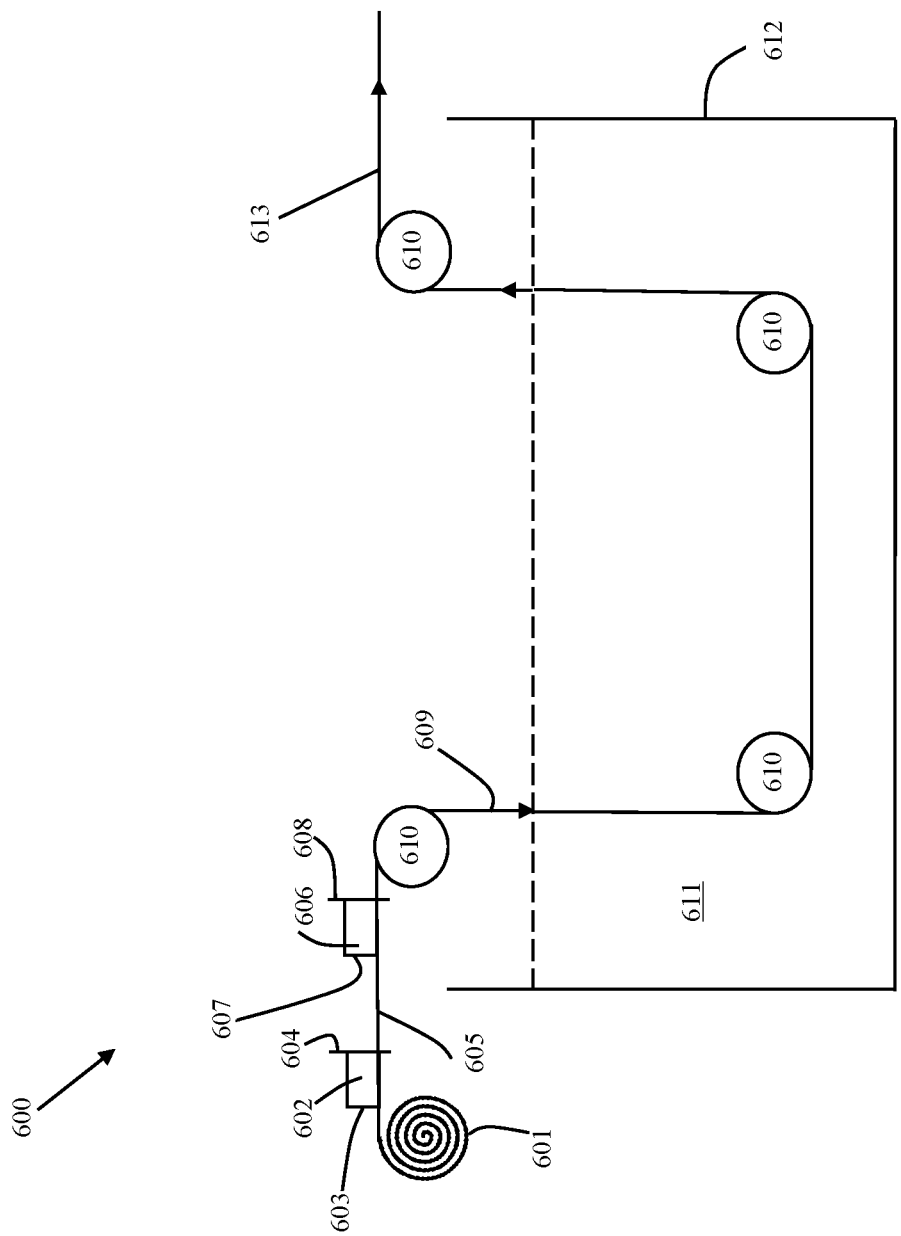
FIG. 6 is a schematic diagram of an apparatus for flat-sheet casting in the production of a microporous flat membrane, according to an example of the present application.

Referring to FIG. 6, an apparatus for flat-sheet casting in the production of a microporous flat membrane, identified by identifier 600, includes a support layer 601 (e.g., a flat-surfaced nonwoven or polymeric plastic sheet or strip), a polymer dope solution 602 stored in tank 603 equipped with a doctor knife or blade 604 at a dispensing side thereof, precipitation fluid 606 containing the additive stored in tank 607 equipped with a doctor knife or blade 608 at a dispensing side thereof, precipitation tank 612 containing a second precipitation fluid in bath 611, and a series of film conveying rollers 610 arranged to pull the support layer 601 to polymer dope solution tank 603, and the film-coated support layer 605 from polymer dope solution tank 603 to precipitation fluid 607, and the precipitation fluid surface-treated film-coated carrier 609 from precipitation fluid tank 607 to and through the second precipitation bath 611 (e.g., water). The resulting polymer film coated carrier 613 including the additive incorporated at the active surface thereof can be rinsed and dried (not shown), e.g., using conventional techniques such as shown in incorporated U.S. Pat. No. 3,691,068. The microporous membrane film formed on the carrier 601, i.e., a microporous polymer membrane, can be permanently attached to the carrier 601, or can be removable from the carrier at any time after applying the precipitation fluid 606 containing the additive to the dope solution-coated carrier. The permanent carrier material can be a nonwoven material or other materials. The removable carrier material can be a polymeric plastic (e.g., thermoplastic or thermoset plastic), such as Mylar, wherein the microporous membrane film can be peelable from the carrier.

Membranes with the additive with limited water solubility at the membrane's active surface, relative to the membrane core, can be fabricated by post-membrane fabrication methods. These post-membrane fabrication methods may include coating, grafting, crosslinking, or a combination of the methods. However, these post-fabrication methods are not desirable because (i) they cannot be easily adapted to current manufacturing processes, (ii) they are not cost-effective, and (iii) leachable and extractable residual byproducts from the post-fabrication methods can lead to toxicity issues. The membrane-forming processes of the present invention can avoid these problems.

The microporous membranes of the present invention can be used, as an option, for dialysis membranes, ultrafiltration membranes, and microfiltration membranes. The dialysis membranes can be, for example, hemodialysis membranes or hemofilters. Semi-permeable membrane filtration is often used in the purification of proteins, microfiltration and ultrafiltration being the most commonly practiced techniques. Microfiltration can be defined as a low pressure membrane filtration process which removes suspended solids and colloids generally larger than 0.1 µm in diameter. Such processes can be used to separate particles or microbes that can be seen with the aid of a microscope such as cells, macrophage, and cellular debris. Ultrafiltration membranes are characterized by pore sizes which enable them to retain macromolecules having a molecular weight ranging from about 500 Daltons to about 1,000,000 Daltons. Ultrafiltration is a low-pressure membrane filtration process which separates solutes in a range of from about 0.01 µm to 0.1 µm. Ultrafiltration can be used for concentrating proteins, and removing bacteria and viruses from a solution. Ultrafiltration also can be used for purification treatments, such as water purification. Dialysis membranes can be ultrafiltration membranes which comprise biocompatible materials, such as polyarylether polymer materials shown herein. When the membranes are hollow fibers, as an option, the hollow fibers can be microporous and capable of withstanding up to about 2,000 psi or more applied pressure without collapse, which refers to pressure applied from outside of the fiber. The hollow fibers, as an option, can have a fiber burst pressure of up to about 500 psi, which refers to pressure applied from the inner lumen side of the fiber.

The present invention further relates to a process of using the microporous membrane for at least one of membrane filtering or solute and/or solvent exchange which can comprise contacting aqueous-based fluid or contacting blood with the microporous membrane described herein. A process for dialysis, blood oxygenation, or blood separation filtering of the present invention can comprise contacting blood with a microporous membrane as described herein.

The present invention will be further clarified by the following examples, which are intended to be only exemplary of the present invention. Unless indicated otherwise, all amounts, percentages, ratios and the like used herein are by weight.

EXAMPLES

Example 1

Initial tests were conducted to study the feasibility of making hollow fiber membranes with an active membrane surface having additive with limited solubility at a composition different from that of the membrane core.

Several commercially obtained polyurethanes were tested as additives and included in the precipitation fluid. The polyurethanes were TECOPHILIC® TG-500 and TG-2000 (Lubrizol LifeScience Polymers). These are water-insoluble hydrogel grade polyurethane materials that are soluble in water-polar aprotic solvent mixtures. Water absorption, solubility in polar aprotic solvent (dimethylacetamide), and solubility in water properties were measured for these polyurethane additives, which are shown in Table 1.

TABLE 1

| Hydrogel Grade Polyurethanes | Water Absorption (wt %) | Solubility in water - DMAC mixture* (at room temperature) | Solubility in water (at room temperature) |
|---|---|---|---|
| TG-500 | 500 | >100 ppm | Not soluble |
| TG-2000 | 900 | >100 ppm | Not soluble |

*Water composition is 40 wt %

Feasibility studies were conducted based on wet phase inversion fiber spinning and fabrication of a dialyzer similar in membrane area to that of a control dialyzer, which was a commercial polysulfone dialyzer product.

Different precipitation fluids were prepared having a composition of 61 wt % dimethylacetamide and 39 wt % water, and a varied amount of TG-2000 polyurethane additive, based on total weight of the precipitation fluid. The amount of TG-2000 additive was varied in different test runs at 250 ppm, 500 ppm, 750 ppm, and 1,000 ppm, based on concentration in the water-polar aprotic solvent mixture of the precipitation fluid. Polymer dope solution was used that was a typical composition that is used to make hollow fiber membranes for dialyzers, which contained polyethersulfone, polyvinylpyrrolidone and dimethylacetamide, and no water.

A wet-spinning spinneret was used for spinning hollow fibers, wherein the indicated polymer dope solution containing the fiber forming polymer and organic solvent were pumped to an annular extrusion spinneret having concentric tubes. The precipitating fluid was pumped through the hollow core so that the precipitating solution emerged from the core tip and made contact with the inner surface of the hollow fiber configuration that was made up of the extruded polymer dope solution. A typical ratio of the volumes of precipitating fluid to polymer dope solution was used. The outer diameter of the hollow fibers formed was about 250 μm, and the thickness of the membrane was about 35 μm.

A summary of the results of this feasibility study, which compares the general feasibility of fiber spinning, urea clearance performance, pore size distribution, and steaming potential of the membrane's active surface of the hollow fibers made with the polyurethane additive included in the precipitation fluid as compared to the commercial product, is provided in Table 2.

TABLE 2

| Results | Outcome |
|---|---|
| Water-insoluble polyurethane used in the precipitation fluid | 250, 500, 750 and 1,000 ppm of TG-2000 |
| Fiber spinning | Demonstrated the feasibility |
| Clearance performance | Similar to that of control |
| Pore size distribution of the membrane | Similar to that of control |
| Steaming potential of the membrane's active surface | Close to neutral compared to the control |

Example 2

Tests were performed to study platelet reduction performance of a dialyzer using hollow fiber membranes made by wet phase inversion fiber spinning as in Example 1 with two different ppm amounts of TG-2000 additive used in the precipitation fluid, in comparison to a control, which was a control dialyzer with no TG-2000 additive.

Whole blood simulations were performed using heparinized human blood following the ISO 10993-4 guidelines. Results of the study are shown in Table 3. All platelet reduction data is normalized to the control. The test sample data was compared to the 100% control regarding the percentage of platelet reduction. The 100 ppm and 1000 ppm amounts of TG-2000 shown in Table 3 are based on the additive concentration in the water-polar aprotic solvent mixture of the precipitation fluid. In each case, the dialyzers were primed by filling and recirculating saline on the blood side of the dialyzer for 10 minutes and filling the dialysate side with saline without circulation. This is referred to as standard in vitro test priming.

TABLE 3

| Sample | Dialyzer | % Platelet Reduction | Mean ± SD |
|---|---|---|---|
| Control | Control | 100 | N/A |
| 1 | 100 ppm of TG2000 additive in precipitation fluid | 108.5 | 102 ± 8.5 |
| 2 | Same as 1 | 92.7 | 102 ± 8.5 |
| 3 | Same as 1 | 106.2 | 102 ± 8.5 |
| 4 | 1000 ppm of TG2000 additive in precipitation fluid | 41.1 | 41.5 ± 11.3 |
| 5 | Same as 4 | 53.0 | 41.5 ± 11.3 |
| 6 | Same as 4 | 30.4 | 41.5 ± 11.3 |

The results for 100 ppm additive had a mean value for platelet reduction which was slightly greater than the control, whereas the results for 1000 ppm additive had a mean value much lower than the control. As shown in the Table above, the microporous membrane containing the additive can have a lower blood platelet reduction relative to a microporous membrane without the additive but otherwise is the same. The microporous membrane containing the additive can have at least a 30% lower blood platelet reduction relative to the microporous membrane without the additive.

Example 3

Tests were performed to study platelet reduction performance of a dialyzer using hollow fiber membranes made by wet phase inversion fiber spinning as in Example 1 with standard and prolonged priming procedures, in comparison to a control. In this example, the control was a dialyzer with no TG-2000 additive.

Dialyzers were primed by filling and recirculating saline on the blood side of the dialyzer for 10 minutes and filling the dialysate side with saline without circulation (standard in vitro test priming). For prolonged priming, after the 10 minute recirculation, the recirculating saline was stopped and the blood and dialysate ports of the dialyzer were capped. The dialyzer then remained closed for an additional 16 hours in the incubator at 37° C. with the blood and dialysate sides completely filled with saline.

The following procedure was used to measure platelet reduction in the dialyzers. Whole blood simulations were performed using heparinized human blood following ISO 10993-4 guidelines. During collection of human blood, 1.5 units of heparin was added to 500 ml of fresh blood and stored in 37° C. incubator until use. The complete test setup for measuring platelet reduction of test and control dialyzers was placed in an incubator at 37° C. Test and control dialyzers were tested side by side for platelet reduction, following the same priming and test procedures. Dialyzers were first primed with either a standard or a prolonged priming procedure. At the time of testing, the collected blood was divided into 250 ml blood bags and used with each of the control and test dialyzer pairs. Initial blood samples from each of the blood bags were collected for testing. These samples are referred to as PRE samples. To begin the platelet reduction test, saline on the blood side of the primed dialyzers was replaced with the collected heparinized blood. Blood circulation was continued at 300 ml/min throughout the test period while the dialysate side was filled with saline without circulation. Blood samples were collected at intervals of 5, 15, 30 and 60 minutes from the sampling port as blood leaves the dialyzers. The collected samples were analyzed for platelet count following ISO 10993-4 guidelines using a reproducible test method. Platelet count of the samples collected at different test intervals for each dialyzer was integrated over the test period of 5 to 60 minutes to calculate platelet count over the test period. Platelet count of PRE sample for each dialyzer was normalized with the platelet count of the test period (i.e., 5 to 60 min) in order to measure platelet reduction of the dialyzer. Platelet reduction of the test sample was then normalized with the platelet reduction of the control dialyzer. Table 4 and Table 5 summarize the results.

TABLE 4

| Sample | Dialyzer | Priming Procedure | % Platelet Reduction | Mean ± SD |
|---|---|---|---|---|
| Control | Control | Standard | 100 | N/A |
| 4 | 1000 ppm of TG2000 additive in precipitation fluid | | 41.1 | 41.5 ± 11.3 |
| 5 | Same as 4 | | 53.0 | |
| 6 | Same as 4 | | 30.4 | |
| Control | Control | Prolonged | 100 | N/A |
| 7 | Same as 4 | | 35.7 | 34.7 ± 1.1 |
| 8 | Same as 4 | | 33.5 | |
| 9 | Same as 4 | | 35.1 | |

TABLE 5

| Sample | Dialyzer | Priming Duration | Min % Platelet Reduction | Max % Platelet Reduction | Mean ± SD |
|---|---|---|---|---|---|
| Control | Control (no additive) | Standard | 100 | 100 | N/A |
| Test Sample | 1000 ppm of TG2000 additive in precipitation fluid | Standard | 30.4 | 53.0 | 41.5 ± 11.3 (n = 3) |
| Control | Control (no additive) | Standard | 100 | 100 | N/A |
| Test Sample | 1000 ppm of TG2000 additive in precipitation fluid | Prolonged | 33.5 | 35.7 | 34.7 ± 1.1 (n = 3) |

As shown in Tables 4 and 5, prolonged priming of the dialyzers reduced the mean as well as the standard deviation of platelet reduction, normalized to the control, relative to standard priming. In addition, the standard deviation seen with prolonged priming was surprisingly low, suggesting that prolonged priming dramatically and unexpectedly improves reproducibility between membranes in terms of hemocompatibility.

The present invention includes the following aspects/embodiments/features in any order and/or in any combination:

1. The present invention relates to a method for making a microporous membrane, comprising:
   a) contacting polymer dope solution with precipitation fluid to precipitate the polymer dope solution to form a microporous membrane having a core and at least one surface, wherein the polymer dope solution comprises at least one polymer and at least one organic solvent, the precipitation fluid comprises additive and water-polar aprotic solvent mixture, wherein the additive itself has (i) low water solubility, (ii) hydrophilic properties, and (iii) solubility in the water-polar aprotic solvent mixture;
   b) rinsing the microporous membrane; and
   c) drying the rinsed microporous membrane;
   wherein at least a portion of the additive is delivered during at least one of a), b) and c) to the at least one surface of the microporous membrane where the additive is coated, embedded, or both to provide an active surface of the microporous membrane containing the additive at a first composition in the active surface which is different from a second composition of the core.

2. The method of any preceding or following embodiment/feature/aspect, wherein the membrane has a higher concentration of the additive in the active surface compared to a non-active region thereof.

3. The method of any preceding or following embodiment/feature/aspect, further comprising controlling the amount of first composition of the active surface by controlling the ratio of the precipitating fluid to the polymer dope solution.

4. The method of any preceding or following embodiment/feature/aspect, wherein the first composition of the active surface contains a higher volumetric concentration of the additive compared to the second composition of the core.

5. The method of any preceding or following embodiment/feature/aspect, wherein at least about 10 wt. % of all the additive in the microporous membrane is present in the active surface.

6. The method of any preceding or following embodiment/feature/aspect, wherein microporous membrane has a total thickness and the active surface has an active surface region thickness, wherein the ratio of the active surface region thickness to the total thickness of the membrane is from about 1:2.5 to about 1:5.
7. The method of any preceding or following embodiment/feature/aspect, wherein the active surface has a higher gravimetric density compared to density of the core.
8. The method of any preceding or following embodiment/feature/aspect, wherein the polymer and additive are contained in a same region of the microporous membrane.
9. The method of any preceding or following embodiment/feature/aspect, further comprising, before steps a)-c):
    1) dissolving the at least one polymer in the at least one organic solvent to form the polymer dope solution; and
    2) dissolving the additive in the water-polar aprotic solvent mixture to provide the precipitation fluid.
10. The method of any preceding or following embodiment/feature/aspect, wherein the additive having a solubility of less than 10 wt % in pure water at room temperature (20° C.-23° C.).
11. The method of any preceding or following embodiment/feature/aspect, wherein the additive having a solubility of less than 1 wt % in pure water at room temperature (20° C.-23° C.).
12. The method of any preceding or following embodiment/feature/aspect, wherein the polymer and the additive is a solid at 25° C.
13. The method of any preceding or following embodiment/feature/aspect, wherein the polymer and the additive is in solid particulate form.
14. The method of any preceding or following embodiment/feature/aspect, wherein the polymer dope solution comprises a homogeneous mixture of the at least one polymer and the at least one organic solvent.
15. The method of any preceding or following embodiment/feature/aspect, wherein the additive has a solubility in the water-polar aprotic solvent mixture of at least about 100 ppm.
16. The method of any preceding or following embodiment/feature/aspect, wherein leaching of the additive out of the membrane during steps a), b), and c) is less than about 40 wt % based on the wt % of additive delivered to the membrane from the precipitation fluid.
17. The method of any preceding or following embodiment/feature/aspect, wherein the additive comprises a nitrogen-containing polymer having at least one oxygen-containing moiety.
18. The method of any preceding or following embodiment/feature/aspect, wherein the additive comprises at least one of polyurethane and chitosan.
19. The method of any preceding or following embodiment/feature/aspect, wherein the additive is a hydrogel grade of polyurethane.
20. The method of any preceding or following embodiment/feature/aspect, wherein the additive is aliphatic polyether based hydrogel thermoplastic polyurethane.
21. The method of any preceding or following embodiment/feature/aspect, wherein the additive is chitosan, and the precipitation fluid further comprises at least one weak acid, and wherein the chitosan protonates when co-present with weak acid in the precipitation fluid.
22. The method of any preceding or following embodiment/feature/aspect, wherein the additive is a pore-forming material in the microporous membrane.
23. The method of any preceding or following embodiment/feature/aspect, wherein the precipitation fluid contains at least about 25 wt % water, based on total weight of the precipitation fluid.
24. The method of any preceding or following embodiment/feature/aspect, wherein the polymer dope solution contains less than about 7 wt % water, based on total weight of the polymer dope solution.
25. The method of any preceding or following embodiment/feature/aspect, wherein the at least one polymer in the dope solution is a hydrophobic polymer.
26. The method of any preceding or following embodiment/feature/aspect, wherein the at least one polymer is at least one of polysulfone (PSF), polyethersulfone (PES), polyarylsulfone (PAS), polyarylethersulfone (PAES), polyvinylidene fluoride (PVDF), polyacrylonitrile (PAN), or any copolymer thereof.
27. The method of any preceding or following embodiment/feature/aspect, wherein the polymer dope solution further comprises at least one hydrophilic polymer other than polyurethane or chitosan.
28. The method of any preceding or following embodiment/feature/aspect, wherein the at least one hydrophilic polymer is at least one of polyvinylpyrrolidone (PVP) or polyethylene glycol (PEG).
29. The method of any preceding or following embodiment/feature/aspect, wherein the polymer dope solution further comprises at least one hydrophilic polymer.
30. The method of any preceding or following embodiment/feature/aspect, wherein the organic solvent is a polar aprotic solvent.
31. The method of any preceding or following embodiment/feature/aspect, wherein the organic solvent is at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), or butyrolactone.
32. The method of any preceding or following embodiment/feature/aspect, wherein the polar aprotic solvent of the water-polar aprotic solvent mixture is at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), or butyrolactone.
33. The method of any preceding or following embodiment/feature/aspect, wherein the microporous membrane that is produced is a hollow fiber or a flat sheet membrane.
34. The method of any preceding or following embodiment/feature/aspect, wherein the microporous membrane is primed to a predetermined moisture content or for a predetermined time after step (c).
35. The method of any preceding or following embodiment/feature/aspect, wherein the microporous membrane is a hollow fiber, wherein the contacting in step a) comprises:
    i) extruding the polymer dope solution through an outer ring duct of a spinneret comprising the outer ring duct and an internal hollow core; and ii) simultaneously with i), passing the precipitation fluid through the internal hollow core, wherein the precipitation fluid acts directly on the polymer dope solution after issuing from the spinneret.

36. The method of any preceding or following embodiment/feature/aspect, wherein the spinneret extrudes only a single polymer dope solution during steps i) and ii).

37. The method of any preceding or following embodiment/feature/aspect, wherein the microporous membrane is a flat sheet membrane, wherein the contacting in step a) comprises:
   i) casting the polymer dope solution onto a surface of a carrier using a doctor blade or knife to provide a film-coated carrier, wherein the film is the polymer dope solution;
   ii) exposing the film-coated carrier to a portion of the precipitation fluid which comprises the additive and water-polar aprotic solvent mixture, wherein the exposing comprises spraying the additive mixture directly onto the surface or by casting a second layer of additive mixture on the surface of the film-coated carrier using a doctor blade or knife, or by gravure coating technique wherein the additive mixture effectively initiates the membrane precipitation process; and
   iii) conveying the surface-treated film-coated carrier through a precipitation bath containing a precipitation fluid to provide a microporous membrane containing product to complete the membrane precipitation process.

38. The method of any preceding or following embodiment/feature/aspect, wherein the microporous membrane is permanently attached or removable from the carrier after step ii).

39. The present invention further relates to a microporous membrane made with the method of any of any preceding or following embodiment/feature/aspect.

40. The present invention further relates to a microporous membrane comprising a core and an active surface, wherein the core and the active surface each comprise polymer, and wherein the active surface contains at least one additive at a first composition in the active surface which is different from a second composition of the core, wherein the additive has (i) low water solubility, (ii) hydrophilic properties, and (iii) solubility in water-polar aprotic solvent mixture.

41. The microporous membrane of any preceding or following embodiment/feature/aspect, wherein the first composition of the active surface contains a higher volumetric concentration of the additive compared to the second composition of the core.

42. The microporous membrane of any preceding or following embodiment/feature/aspect, wherein at least about 10 wt % of all the additive in the microporous membrane is present in the active surface.

43. The microporous membrane of any preceding or following embodiment/feature/aspect, wherein membrane has a total thickness and the active surface has an active surface region thickness, wherein the ratio of the active surface region thickness to the total thickness of the membrane is from about 1:2.5 to about 1:5.

44. The microporous membrane of any preceding or following embodiment/feature/aspect, wherein the active surface has a higher gravimetric density compared to density of the core.

45. The microporous membrane of any preceding or following embodiment/feature/aspect, wherein the polymer and additive are contained in a same single layer of the microporous membrane.

46. The microporous membrane of any preceding or following embodiment/feature/aspect, wherein the additive comprises a linear nitrogen-containing polymer having at least one hydroxyl group.

47. The microporous membrane of any preceding or following embodiment/feature/aspect, wherein the additive comprises at least one of polyurethane and chitosan.

48. The microporous membrane of any preceding or following embodiment/feature/aspect, wherein the additive is a hydrogel grade of polyurethane.

49. The microporous membrane of any preceding or following embodiment/feature/aspect, wherein the additive is aliphatic polyether based hydrogel thermoplastic polyurethane.

50. The microporous membrane of any preceding or following embodiment/feature/aspect, wherein the additive is chitosan.

51. The microporous membrane of any preceding or following embodiment/feature/aspect, wherein the microporous membrane is a hollow fiber or a flat sheet membrane.

52. The present invention further relates to a dialyzer comprising the microporous membrane of any preceding or following embodiment/feature/aspect.

53. The present invention further relates to a hemofilter comprising the microporous membrane of any preceding or following embodiment/feature/aspect.

54. The present invention further relates to a process for at least one of membrane filtering or solute and/or solvent exchange comprising contacting aqueous-based fluid with a microporous membrane of any preceding or following embodiment/feature/aspect.

55. A process for at least one of membrane filtering or solute exchange comprising contacting blood with a microporous membrane of any preceding or following embodiment/feature/aspect.

56. A process for dialysis, blood oxygenation, or blood separation filtering comprising contacting blood with a microporous membrane of any preceding or following embodiment/feature/aspect.

57. The microporous membrane of any preceding or following embodiment/feature/aspect, wherein 100% by wt (based on total wt of additive) of the additive is present as a coating on the active surface of the membrane.

58. The method of any preceding or following embodiment/feature/aspect, wherein the method results in 100% by wt (based on total wt of additive) is formed into a coating on the active surface of the membrane.

59. The microporous membrane or method of any preceding or following embodiment/feature/aspect, wherein the additive is a hydrogel.

60. The microporous membrane or method of any preceding or following embodiment/feature/aspect, wherein the additive has the property of being capable of absorbing water or aqueous fluid in amounts ranging from about 20% to 1000% of their dry weight at equilibrium (and e.g. as measured at 25° C.), such as from 20% to 60%, or from 20% to 100%, or from 20% to 150%, or from 20% to 500%, or from 20% to 900%, or from 60% to 100%, or from 60% to 150%, or from 60% to 500%, or from 60% to 900%, or from 60% to 1000%, or from 100% to 150% or from 100% to 900%, or from 100% to 1000%, or from 500% to 900%, or from 500% to 1000%, or even greater than 1000%.

61. The method of any preceding or following embodiment/feature/aspect, wherein the additive itself has a water absorption from 20% to 900% of the weight of the additive in a dry state.

62. A method for making a microporous membrane, comprising:
   a) contacting polymer dope solution with precipitation fluid to precipitate the polymer dope solution to form a microporous membrane having at least one non-active region and at least one surface, wherein the polymer dope solution comprises at least one polymer and at least one organic solvent, the precipitation fluid comprises additive and water-polar aprotic solvent mixture, wherein the additive itself has (i) low water solubility, (ii) hydrophilic properties, and (iii) a water absorption from 20% up to 1000% of the weight of dry additive;
   b) rinsing the microporous membrane; and
   c) drying the rinsed microporous membrane;
wherein at least a portion of the additive is delivered during at least one of a), b) and c) to the at least one surface of the microporous membrane where the additive is coated, embedded, or both to provide an active surface of the microporous membrane containing the additive at a first composition in the active surface which is different from a second composition of the non-active region.

63. A microporous membrane comprising at least one non-active region and at least one active surface, wherein the non-active region and the active surface each comprise polymer, and wherein the active surface contains at least one additive at a first composition in the active surface which is different from a second composition of the non-active region, wherein the additive itself has (i) low water solubility, (ii) hydrophilic properties, (iii) a water absorption from 20% up to 900% of the weight of dry additive.

64. The microporous membrane of any preceding or following embodiment/feature/aspect, wherein the additive has a solubility in a water-dimethylacetamide mixture of at least about 100 ppm.

65. The microporous membrane of any preceding or following embodiment/feature/aspect, wherein the membrane has lower blood platelet reduction relative to the microporous membrane without the additive, as determined with the additive fully saturated with water in whole blood simulations using heparinized human blood in accordance with ISO 10993-4.

66. The microporous membrane of any preceding or following embodiment/feature/aspect, wherein the membrane has a blood platelet reduction of at least 30% relative to the microporous membrane without the additive.

67. The microporous membrane of any preceding or following embodiment/feature/aspect, wherein the first composition of the active surface contains a higher volumetric concentration of the additive compared to the second composition of the active region.

68. The microporous membrane of any preceding or following embodiment/feature/aspect, wherein at least about 10 wt % of all the additive in the microporous membrane is present in the active surface.

69. A microporous membrane comprising at least one non-active region and at least one active surface, wherein the non-active region and the active surface each comprise polymer, and wherein the active surface contains at least one additive at a first composition in the active surface which is different from a second composition of the non-active region, wherein the additive itself has (i) a water absorption from 20% up to 1000% of the weight of dry additive, and (ii) wherein the membrane has a reduced blood platelet reduction relative to the microporous membrane without the additive, as determined with the microporous membrane fully saturated with water in whole blood simulations using heparinized human blood in accordance with ISO 10993-4.

70. The microporous membrane of any preceding or following embodiment/feature/aspect, wherein the membrane has a blood platelet reduction of at least 30% relative to the microporous membrane without the additive.

71. The microporous membrane of any preceding or following embodiment/feature/aspect, wherein the microporous membrane has an improved platelet reduction when fully saturated compared to less than fully saturated.

72. The microporous membrane of any preceding or following embodiment/feature/aspect, wherein the additive itself further has either (i) low water solubility or (ii) hydrophilic properties or both.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A microporous membrane comprising at least one non-active region and at least one active surface, wherein the at least one active surface includes a coating, and wherein the at least one non-active region and the at least one active surface each comprise at least one polymer, and the coating consists essentially of at least one additive, the at least one additive itself is a polymeric additive that has (i) low water solubility, (ii) hydrophilic properties, and (iii) solubility in a water-polar aprotic solvent mixture, and wherein the at least one additive of the coating is diffused towards the at least one non-active region such that a concentration of the at least one additive decreases in a direction from the at least one active surface towards the at least one non-active region.

2. The microporous membrane of claim 1, wherein the microporous membrane includes a core and wherein the at least one active surface has a higher gravimetric density compared to density of the core.

3. The microporous membrane of claim 1, wherein the at least one additive comprises at least one of polyurethane and chitosan.

4. The microporous membrane of claim 1, wherein the at least one additive is a polyurethane hydrogel.

5. The microporous membrane of claim 1, wherein the at least one additive comprises a nitrogen-containing polymer having at least one oxygen-containing moiety.

6. The microporous membrane of claim 1, wherein the at least one additive comprises at least one polyurethane.

7. The microporous membrane of claim 1, wherein the at least one additive has a solubility in the water-polar aprotic solvent mixture of at least about 100 ppm.

8. The microporous membrane of claim 1, wherein at least about 10 wt. % of all the at least one additive in the microporous membrane is present in the at least one active surface.

9. The microporous membrane of claim 1, wherein the microporous membrane has a total thickness and the at least one active surface has an active surface region thickness, wherein the ratio of the active surface region thickness to the total thickness of the microporous membrane is from about 1:2.5 to about 1:5.

10. The microporous membrane of claim 1, wherein the at least one additive has a solubility of less than 10 wt % in pure water at room temperature (20° C.).

11. The microporous membrane of claim 1, wherein the at least one polymer is at least one of polysulfone (PSF), polyethersulfone (PES), polyarylsulfone (PAS), polyarylethersulfone (PAES), polyvinylidene fluoride (PVDF), polyacrylonitrile (PAN), or any copolymer thereof.

12. The microporous membrane of claim 1, wherein the microporous membrane is a hollow fiber.

13. The microporous membrane of claim 1, wherein from about 15 vol % to 99 vol % of all the at least one additive in the microporous membrane is present in the at least one active surface.

14. The microporous membrane of claim 1, wherein the at least one additive in the microporous membrane is present in an amount of at least 0.1 wt % based on weight of said microporous membrane.

15. The microporous membrane of claim 1, wherein 100% by weight of the at least one additive, based on total weight of the at least one additive, is present in the coating.

16. The microporous membrane of claim 1, wherein the coating itself is not formed into a self-supporting membrane structure.

17. A process for dialysis, blood oxygenation, or blood separation filtering comprising contacting blood with the microporous membrane of claim 1.

18. A microporous membrane comprising at least one non-active region and at least one active surface, wherein the at least one active surface includes a coating and wherein the at least one non-active region and the at least one active surface each comprise at least one polymer, and the coating consists essentially of the polymeric at least one additive, the at least one additive itself is a polymeric additive and has (i) a water absorption from 20% up to 1000% of the weight of dry additive, and (ii) wherein the microporous membrane has a reduced blood platelet reduction relative to the microporous membrane without the at least one additive, and wherein the at least one additive of the coating is diffused towards the at least one non-active region such that a concentration of the at least one additive decreases in a direction from the at least one active surface towards the at least one non-active region.

19. The microporous membrane of claim 18, wherein the microporous membrane has a blood platelet reduction of at least 30% relative to the microporous membrane without the at least one additive.

20. The microporous membrane of claim 18, wherein the microporous membrane has an improved platelet reduction when fully saturated compared to less than fully saturated.

21. The microporous membrane of claim 18, wherein the at least one additive comprises at least one polyurethane.

22. The microporous membrane of claim 18, wherein 100% by weight of the at least one additive, based on total weight of the at least one additive, is present in the coating.

23. The microporous membrane of claim 18, wherein the coating itself is not formed into a self-supporting membrane structure.

* * * * *